United States Patent
Shin et al.

(10) Patent No.: US 9,242,990 B2
(45) Date of Patent: Jan. 26, 2016

(54) COMPOUND, NOVEL MIXTURE, PHOTOSENSITIVE RESIN COMPOSITION, AND COLOR FILTER

(71) Applicant: Samsung SDI Co., Ltd., Yongin-si (KR)

(72) Inventors: Myoung-Youp Shin, Suwon-si (KR); Won-Jung Kim, Suwon-si (KR); Kyung-Soo Moon, Suwon-si (KR); Chae-Won Pak, Suwon-si (KR); Eui-Soo Jeong, Suwon-si (KR); Ki-Wook Hwang, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 0 days.

(21) Appl. No.: 14/528,125

(22) Filed: Oct. 30, 2014

(65) Prior Publication Data

US 2015/0322077 A1 Nov. 12, 2015

(30) Foreign Application Priority Data

May 12, 2014 (KR) .................. 10-2014-0056655

(51) Int. Cl.
| | | |
|---|---|---|
| *G02B 5/20* | (2006.01) | |
| *C07D 487/22* | (2006.01) | |
| *G03F 7/00* | (2006.01) | |
| *C09B 47/04* | (2006.01) | |
| *G02B 5/22* | (2006.01) | |

(52) U.S. Cl.
CPC .............. *C07D 487/22* (2013.01); *C09B 47/04* (2013.01); *G02B 5/223* (2013.01); *G03F 7/0007* (2013.01)

(58) Field of Classification Search
CPC ....... G03F 7/0007; G03F 7/105; C09B 47/04; C09B 487/22; G02B 5/223
USPC ............................ 430/7, 270.1; 540/137, 140
See application file for complete search history.

(56) References Cited

U.S. PATENT DOCUMENTS

| 5,380,842 | A * | 1/1995 | Itoh et al. ................... 540/128 |
|---|---|---|---|
| 5,998,091 | A | 12/1999 | Suzuki |
| 6,033,813 | A | 3/2000 | Endo et al. |
| 6,733,935 | B2 | 5/2004 | Kishimoto et al. |
| 7,517,619 | B2 | 4/2009 | Hosaka et al. |

FOREIGN PATENT DOCUMENTS

| JP | 06-041458 A | 2/1994 |
|---|---|---|
| JP | 07-140654 A | 6/1995 |
| JP | 10-254133 A | 9/1998 |
| KR | 10-2002-0015650 A | 2/2002 |
| KR | 10-2005-0020653 A | 3/2005 |
| KR | 10-1999-0007097 A | 8/2005 |
| KR | 10-2009-0106226 A | 10/2009 |
| KR | 10-2010-0078845 A | 7/2010 |
| KR | 10-2010-0080142 A | 7/2010 |
| TW | 201319741 A | 5/2013 |
| TW | 201321802 A | 6/2013 |
| TW | 201337457 A | 9/2013 |

OTHER PUBLICATIONS

Al-Raqa et al. "Preparation and optical properties of novel symmetrical hexadecachlorinatedphthalocyaninato zinc(II) spin coated thin films", Polyhedron 27 (2008) 1256-1261, Feb. 2008.*
Atsay et al. "A new hexadeca substituted non-aggregating zinc phthalocyanine", Dyes and pigments 100 (2014) 177-183, Sep. 2013.*
U.S. Appl. No. 14/593,243, filed Jan. 9, 2015, pp. 1-64.
Search Report in counterpart Taiwanese Application No. 103142078 dated Nov. 5, 2015, pp. 1.
Kurt et al., "Synthesis and photophysical properties of novel hexadeca-substituted phthalocyanines bearing three different groups", Journal of Organometallic Chemistry, vol. 754, 2014, pp. 8-15.
Search Report in commonly owned Taiwanese Application No. 104105204 dated Sep. 18, 2015, pp. 1.

* cited by examiner

*Primary Examiner* — John A McPherson
(74) *Attorney, Agent, or Firm* — Additon, Higgins & Pendleton, P.A.

(57) ABSTRACT

A compound is represented by the following Chemical Formula 1, wherein in Chemical Formula 1, each substituent is the same as defined in the detailed description:

[Chemical Formula 1]

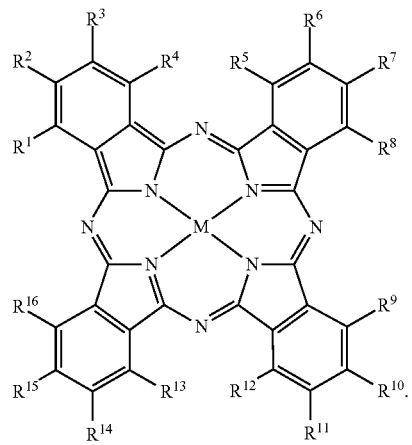

13 Claims, No Drawings

COMPOUND, NOVEL MIXTURE, PHOTOSENSITIVE RESIN COMPOSITION, AND COLOR FILTER

CROSS-REFERENCE TO RELATED APPLICATION

This application claims priority to and the benefit of Korean Patent Application No. 10-2014-0056655 filed in the Korean Intellectual Property Office on May 12, 2014, the entire disclosure of which is incorporated herein by reference.

FIELD OF THE INVENTION

This disclosure relates to a novel compound, a novel mixture, and a photosensitive resin composition and color filter including the compound or mixture.

BACKGROUND

A color filter manufactured by using a pigment-type photosensitive resin composition has a limit in terms of luminance and a contrast ratio caused by a pigment particle size. In addition, an imaging sensor device requires a smaller dispersion particle size to form a fine pattern. In order to satisfy the requirement, there have been attempts to manufacture a color filter having improved color characteristics such as luminance, a contrast ratio and the like using a dye forming no particle instead of a pigment in the photosensitive resin composition.

Accordingly, there is a need for an appropriate compound as the dye used to manufacture the photosensitive resin composition.

SUMMARY

One embodiment provides a novel compound.
Another embodiment provides a novel mixture.
Yet another embodiment provides a photosensitive resin composition including the compound or the mixture.
Still another embodiment provides a color filter manufactured using the photosensitive resin composition.
One embodiment provides a compound represented by the following Chemical Formula 1:

[Chemical Formula 1]

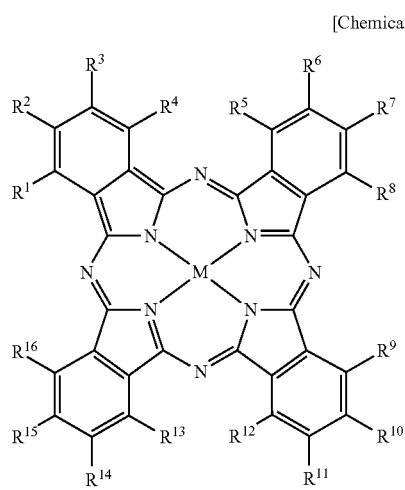

wherein, in the above Chemical Formula 1,
M is Cu, Zn, Co, or Mo, $R^1$ to $R^{16}$ are the same or different and are each independently hydrogen, halogen, substituted or unsubstituted C1 to C20 alkyl, substituted or unsubstituted C1 to C20 alkoxy, substituted or unsubstituted C6 to C20 aryl, or substituted or unsubstituted C6 to C20 aryloxy, wherein at least one of $R^1$ to $R^{16}$ is substituted or unsubstituted C1 to C20 alkoxy, and at least one of $R^1$ to $R^{16}$ is substituted or unsubstituted C6 to C20 aryloxy.

In exemplary embodiments, $R^1$ to $R^{16}$ may be independently halogen, substituted or unsubstituted C1 to C20 alkoxy, and/or substituted or unsubstituted C6 to C20 aryloxy.

Examples of the C1 to C20 alkoxy may include without limitation methoxy, ethoxy, propoxy, butoxy, pentyloxy, hexyloxy, heptyloxy, octyloxy, nonyloxy, and/or decyloxy.

The C6 to C20 aryloxy may be represented by the following Chemical Formula 2:

[Chemical Formula 2]

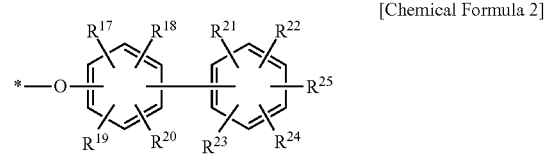

wherein, in the above Chemical Formula 2,
$R^{17}$ to $R^{25}$ are the same or different and are each independently hydrogen, halogen, or substituted or unsubstituted C1 to C8 alkyl.

In exemplary embodiments, at least one of $R^1$ to $R^4$ may be substituted or unsubstituted C6 to C20 aryloxy, at least one of $R^5$ to $R^8$ may be substituted or unsubstituted C6 to C20 aryloxy, at least one of $R^9$ to $R^{12}$ may be substituted or unsubstituted C6 to C20 aryloxy, and at least one of $R^{13}$ to $R^{16}$ may be substituted or unsubstituted C1 to C20 alkoxy.

In exemplary embodiments, at least one of $R^1$ to $R^4$ may be substituted or unsubstituted C6 to C20 aryloxy, at least one of $R^5$ to $R^8$ may be substituted or unsubstituted C1 to C20 alkoxy, at least one of $R^9$ to $R^{12}$ may be substituted or unsubstituted C1 to C20 alkoxy, and at least one of $R^{13}$ to $R^{16}$ may be substituted or unsubstituted C1 to C20 alkoxy.

In exemplary embodiments, at least one of $R^1$ to $R^4$ may be substituted or unsubstituted C6 to C20 aryloxy, at least one of $R^5$ to $R^8$ may be substituted or unsubstituted C1 to C20 alkoxy, at least one of $R^9$ to $R^{12}$ may be substituted or unsubstituted C6 to C20 aryloxy, and at least one of $R^{13}$ to $R^{16}$ may be substituted or unsubstituted C1 to C20 alkoxy.

In exemplary embodiments, at least one of $R^1$ to $R^4$ may be substituted or unsubstituted C6 to C20 aryloxy, at least one of $R^5$ to $R^8$ may be substituted or unsubstituted C6 to C20 aryloxy, at least one of $R^9$ to $R^{12}$ may be substituted or unsubstituted C1 to C20 alkoxy, and at least one of $R^{13}$ to $R^{16}$ may be substituted or unsubstituted C1 to C20 alkoxy.

The compound may be represented by one or more of the following Chemical Formulae 3 to 6.

[Chemical Formula 3]
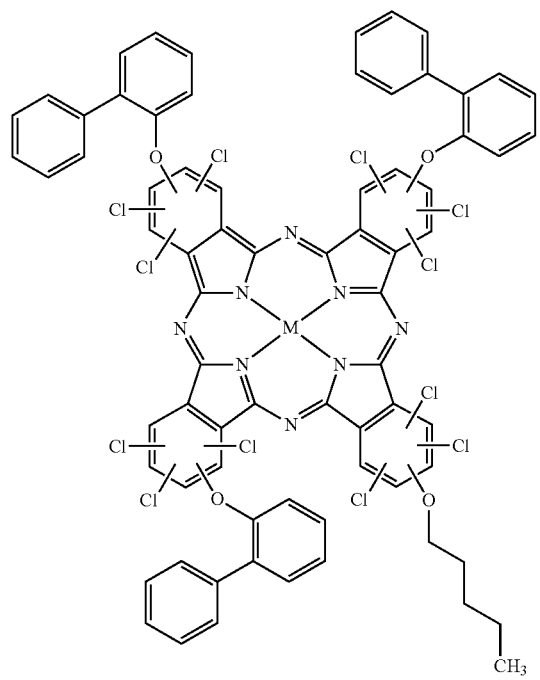
[Chemical Formula 4]
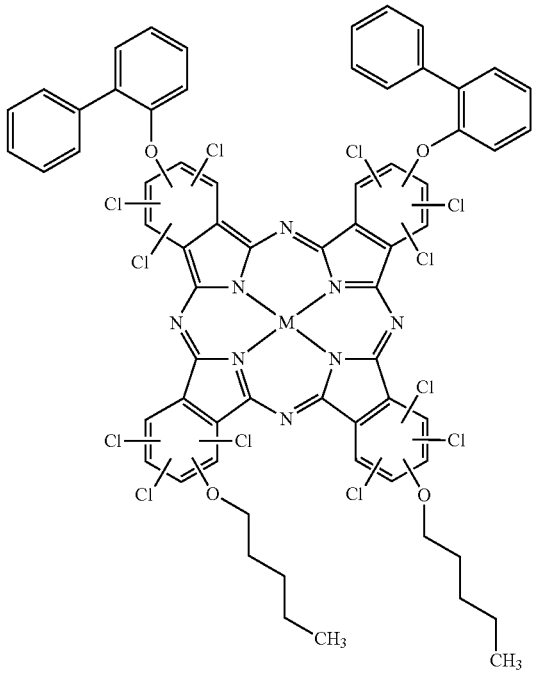
[Chemical Formula 5]
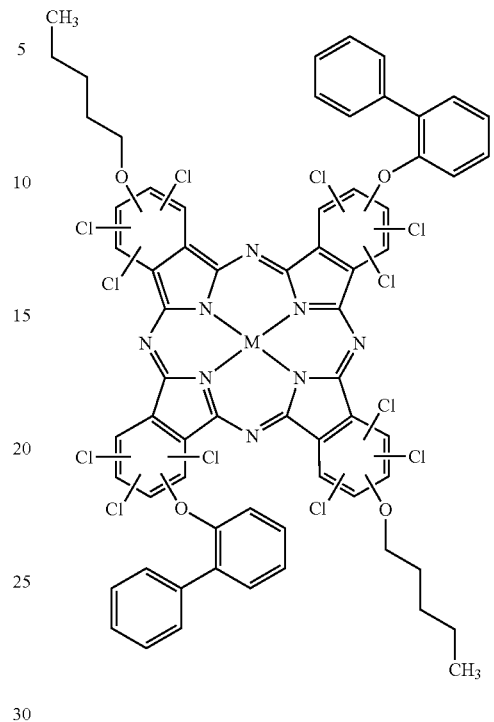
[Chemical Formula 6]
In the Chemical Formulae 3 to 6, M may be Cu, Zn, Co, or Mo.
The compound may be a green dye.
Another embodiment provides a mixture of at least two or more compounds of compounds represented by the above Chemical Formulae 3 to 6.

Yet another embodiment provides a photosensitive resin composition including the compound or the mixture.

Still another embodiment provides a color filter manufactured using the photosensitive resin composition.

The compound or mixture according to one embodiment can have excellent green spectral characteristics, a high molar extinction coefficient, and/or excellent solubility for an organic solvent and thus, may be used as a dye during preparation of a photosensitive resin composition for a green color filter, and a color filter including the dye may have excellent luminance and contrast ratio.

DETAILED DESCRIPTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

As used herein, when a specific definition is not otherwise provided, the term "substituted" refers to one substituted with a substituent including halogen (F, Br, Cl, or I), a hydroxy group, a nitro group, a cyano group, an amino group ($NH_2$, $NH(R^{200})$ or $N(R^{201})(R^{202})$, wherein $R^{200}$, $R^{201}$ and $R^{202}$ are the same or different and are each independently C1 to C10 alkyl), an amidino group, a hydrazine group, a hydrazone group, a carboxyl group, substituted or unsubstituted alkyl, substituted or unsubstituted alkenyl, substituted or unsubstituted alkynyl, substituted or unsubstituted alkoxy, a substituted or unsubstituted alicyclic organic group, substituted or unsubstituted aryl and/or a substituted or unsubstituted heterocyclic group instead of a functional group of the present invention.

As used herein, when a specific definition is not otherwise provided, the term "alkyl" refers to C1 to C20 alkyl, for example C1 to C15 alkyl, the term "cycloalkyl" refers to C3 to C20 cycloalkyl, for example C3 to C18 cycloalkyl, the term "alkoxy" refers to C1 to C20 alkoxy, for example C1 to C18 alkoxy, the term "aryl" refers to C6 to C20 aryl, for example C6 to C18 aryl, the term "alkenyl" refers to C2 to C20 alkenyl, for example C2 to C18 alkenyl, the term "alkylene" refers to C1 to C20 alkylene, for example C1 to C18 alkylene, and the term "arylene" refers to C6 to C20 arylene, for example C6 to C16 arylene.

As used herein, when a specific definition is not otherwise provided, the term "aliphatic organic group" refers to C1 to C20 alkyl, C2 to C20 alkenyl, C2 to C20 alkynyl, C1 to C20 alkylene, C2 to C20 alkenylene or C2 to C20 alkynylene, for example C1 to C15 alkyl, C2 to C15 alkenyl, C2 to C15 alkynyl, C1 to C15 alkylene, C2 to C15 alkenylene, or C2 to C15 alkynylene, the term "alicyclic organic group" refers to C3 to C20 cycloalkyl, C3 to C20 cycloalkenyl, C3 to C20 cycloalkynyl, C3 to C20 cycloalkylene, C3 to C20 cycloalkenylene, or C3 to C20 cycloalkynylene, for example C3 to C15 cycloalkyl, C3 to C15 cycloalkenyl, C3 to C15 cycloalkynyl, C3 to C15 cycloalkylene, C3 to C15 cycloalkenylene or C3 to C15 cycloalkynylene, the term "aromatic organic group" refers to C6 to C20 aryl or C6 to C20 arylene, for example C6 to C16 aryl or C6 to C16 arylene, the term "heterocyclic group" refers to C2 to C20 cycloalkyl, C2 to C20 cycloalkylene, C2 to C20 cycloalkenyl, C2 to C20 cycloalkenylene, C2 to C20 cycloalkynyl, C2 to C20 cycloalkynylene, C2 to C20 heteroaryl or C2 to C20 heteroarylene that include 1 to 3 hetero atoms including O, S, N, P, Si, or a combination thereof in a ring, for example C2 to C15 cycloalkyl, C2 to C15 cycloalkylene, C2 to C15 cycloalkenyl, C2 to C15 cycloalkenylene, C2 to C15 cycloalkynyl, C2 to C15 cycloalkynylene, C2 to C15 heteroaryl, or C2 to C15 heteroarylene that include 1 to 3 hetero atoms including O, S, N, P, Si, or a combination thereof in a ring.

As used herein, when a definition is not otherwise provided, the term "combination" refers to mixing or copolymerization. In addition, "copolymerization" refers to block copolymerization to random copolymerization, and "copolymer" refers to a block copolymer to a random copolymer.

In the Chemical Formula of the present specification, unless a specific definition is otherwise provided, hydrogen is bonded at a position when a chemical bond is not drawn where a bond would otherwise appear.

As used herein, when specific definition is not otherwise provided, "*" indicates a point where the same or different atom or Chemical Formula is linked.

One embodiment provides a compound represented by the following Chemical Formula 1:

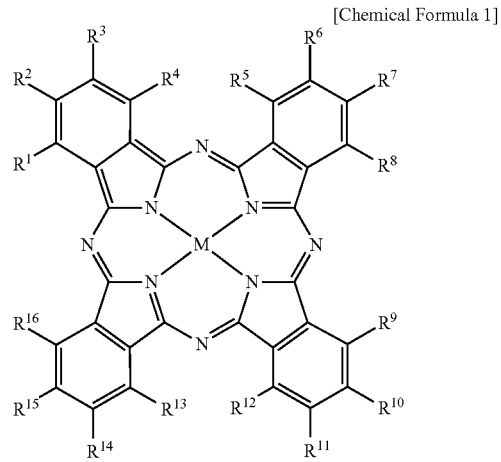

[Chemical Formula 1]

wherein in the above Chemical Formula 1,
M is Cu, Zn, Co, or Mo,
$R^1$ to $R^{16}$ are the same or different and are each independently hydrogen, halogen, substituted or unsubstituted C1 to C20 alkyl, substituted or unsubstituted C1 to C20 alkoxy, substituted or unsubstituted C6 to C20 aryl, or substituted or unsubstituted C6 to C20 aryloxy, wherein at least one of $R^1$ to $R^{16}$ is substituted or unsubstituted C1 to C20 alkoxy, and wherein at least one of $R^1$ to $R^{16}$ is substituted or unsubstituted C6 to C20 aryloxy.

The compound represented by the above Chemical Formula 1 can have excellent green spectral characteristics and a high molar extinction coefficient. Furthermore, the compound represented by the above Chemical Formula 1 necessarily includes an alkoxy group and an aryloxy group and may have excellent solubility for an organic solvent.

In an exemplary embodiment, M may be Zn.

In an exemplary embodiment, $R^1$ to $R^{16}$ may be the same or different and may be each independently halogen, substituted or unsubstituted C1 to C20 alkoxy, or substituted or unsubstituted C6 to C20 aryloxy, wherein at least one of $R^1$ to $R^{16}$ is substituted or unsubstituted C1 to C20 alkoxy, and wherein at least one of $R^1$ to $R^{16}$ is substituted or unsubstituted C6 to C20 aryloxy.

Examples of the C1 to C20 alkoxy may include methoxy, ethoxy, propoxy, butoxy, pentyloxy, hexyloxy, heptyloxy, octyloxy, nonyloxy, and/or decyloxy, and the C6 to C20 aryloxy may be represented by the following Chemical Formula 2. For example, the C1 to C20 alkoxy may be pentyloxy.

[Chemical Formula 2]

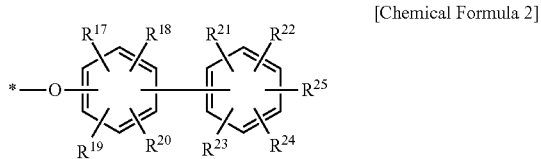

In the above Chemical Formula 2, $R^{17}$ to $R^{25}$ are the same or different and are each independently hydrogen, halogen, or substituted or unsubstituted C1 to C8 alkyl. For example, $R^{17}$ to $R^{25}$ may be all hydrogen.

In exemplary embodiments, in the compound represented by the above Chemical Formula 1, at least one of $R^1$ to $R^4$ may be substituted or unsubstituted C6 to C20 aryloxy, at least one of $R^5$ to $R^8$ may be substituted or unsubstituted C6 to C20 aryloxy, at least one of $R^9$ to $R^{12}$ may be substituted or unsubstituted C6 to C20 aryloxy, and at least one of $R^{13}$ to $R^{16}$ may be substituted or unsubstituted C1 to C20 alkoxy.

In exemplary embodiments, in the compound represented by the above Chemical Formula 1, at least one of $R^1$ to $R^4$ may be substituted or unsubstituted C6 to C20 aryloxy, at least one of the $R^5$ to $R^8$ may be substituted or unsubstituted C1 to C20 alkoxy, at least one of $R^9$ to $R^{12}$ may be substituted or unsubstituted C1 to C20 alkoxy, and at least one of $R^{13}$ to $R^{16}$ may be substituted or unsubstituted C1 to C20 alkoxy.

In exemplary embodiments, iln the compound represented by the above Chemical Formula 1, at least one of $R^1$ to $R^4$ may be substituted or unsubstituted C6 to C20 aryloxy, at least one of $R^5$ to $R^8$ may be substituted or unsubstituted C1 to C20 alkoxy, at least one of $R^9$ to $R^{12}$ may be substituted or unsubstituted C6 to C20 aryloxy, and at least one of $R^{13}$ to $R^{16}$ may be substituted or unsubstituted C1 to C20 alkoxy.

In exemplary embodiments, in the compound represented by the above Chemical Formula 1, at least one of $R^1$ to $R^4$ may be substituted or unsubstituted C6 to C20 aryloxy, at least one of $R^5$ to $R^8$ may be substituted or unsubstituted C6 to C20 aryloxy, at least one of $R^9$ to $R^{12}$ may be substituted or unsubstituted C1 to C20 alkoxy, and at least one of $R^{13}$ to $R^{16}$ may be substituted or unsubstituted C1 to C20 alkoxy.

For example, the compound may be represented by one or more of the following Chemical Formulae 3 to 6.

[Chemical Formula 3]

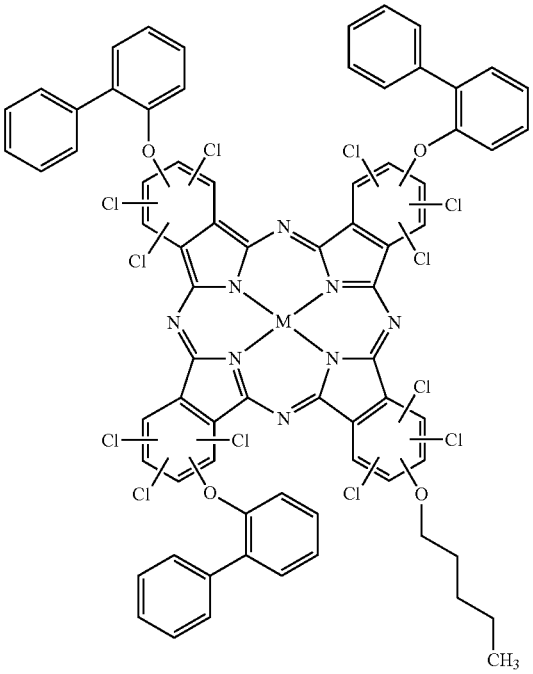

[Chemical Formula 4]

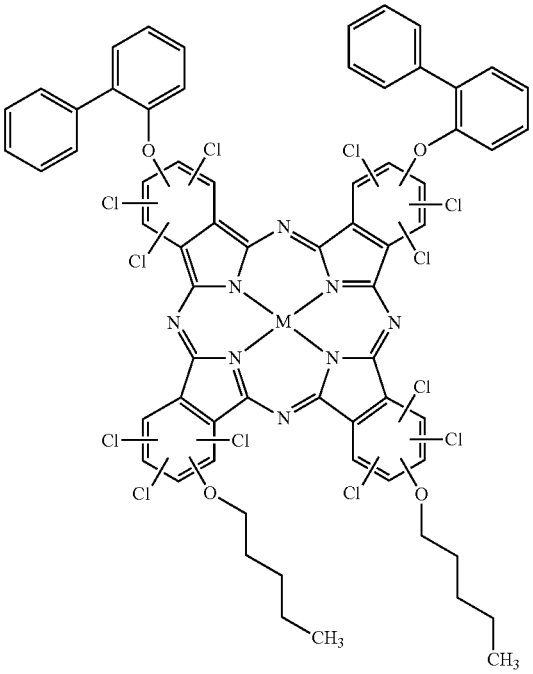

[Chemical Formula 5]

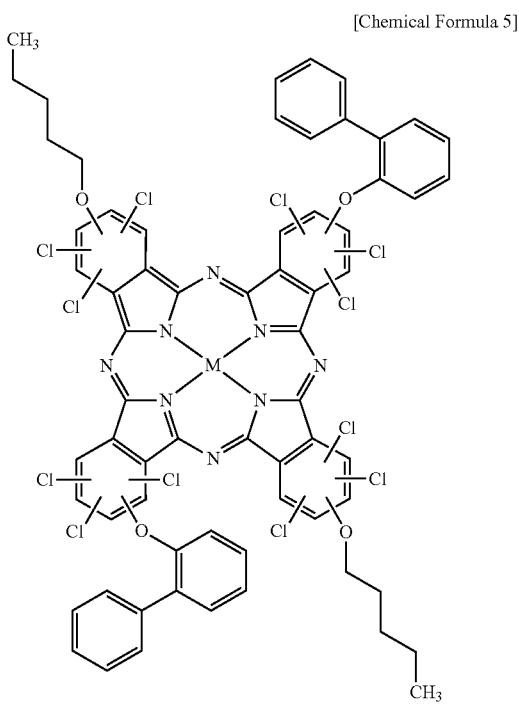

[Chemical Formula 6]

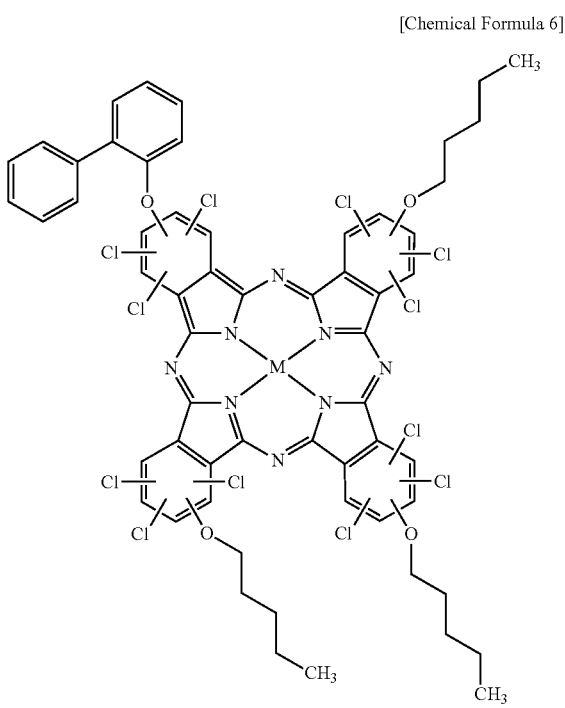

In the above Chemical Formulae 3 to 6, M may be Cu, Zn, Co, or Mo. For example, M may be Zn.

Since the compound according to one embodiment may realize a clearer color even in a smaller amount, a display device having excellent color characteristics such as luminance, a contrast ratio and the like may be manufactured by using the compound as a colorant. For example, the compound may be a colorant, for example a dye, for example a green dye.

In general, a dye is the most expensive among the components used in a color filter. Large amounts of the expensive dye may be required to accomplish a desired effect, for example, high luminance, a high contrast ratio or the like. This, in turn, can increase the unit cost of production. However, when the compound according to one embodiment is used as a dye in a color filter, the compound may accomplish excellent color characteristics such as high luminance, a high contrast ratio and the like even though used in a small amount and thus can reduce the unit cost of production.

According to one embodiment, a mixture of at least two or more compounds of compounds represented by the above Chemical Formulae 3 to 6 is provided.

According to one embodiment, a photosensitive resin composition including the compound or the mixture according to the above embodiment is provided.

For example, the photosensitive resin composition can include the compound or the mixture according to the above embodiment, an alkali soluble resin, a photopolymerizable compound, a photopolymerization initiator, and a solvent.

The compound or mixture according to one embodiment may play a role of a colorant, for example, a dye and specifically, a green dye, and can realize excellent color characteristics.

The photosensitive resin composition may further include one or more other dye compounds other than (in addition to) the compound according to one embodiment as a colorant.

The photosensitive resin composition may include the compound of Chemical Formula 1 or a mixture thereof in an amount of about 0.1 wt % to about 30 wt % based on the total amount (total weight, 100 wt %) of the photosensitive resin composition. In some embodiments, the photosensitive resin composition may include the compound or mixture thereof in an amount of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt %. Further, according to some embodiments of the present invention, the amount of the compound of Chemical Formula 1 or mixture thereof can be in a range from about any of the foregoing amounts to about any other of the foregoing amounts.

In addition, the photosensitive resin composition may further include a pigment. In this case, the pigment may be included in a form of pigment dispersion.

The alkali soluble resin may be an acrylic-based resin.

The acrylic-based resin can be a copolymer of a first ethylenic unsaturated monomer and a second ethylenic unsaturated monomer that is copolymerizable therewith, and includes at least one acrylic-based repeating unit.

The first ethylenic unsaturated monomer is an ethylenic unsaturated monomer including at least one carboxyl group. Examples of the first ethylenic unsaturated monomer include without limitation (meth)acrylic acid, maleic acid, itaconic acid, fumaric acid, and the like, and combinations thereof.

The acrylic-based resin may include the first ethylenic unsaturated monomer in an amount of about 5 to about 50 wt %, for example about 10 to about 40 wt %, based on the total amount (total weight, 100 wt %) of the acrylic-based resin.

Examples of the second ethylenic unsaturated monomer may include without limitation aromatic vinyl compounds such as styrene, α-methylstyrene, vinyl toluene, vinylbenzylmethylether and the like; unsaturated carboxylate ester compounds such as methyl(meth)acrylate, ethyl(meth)acrylate, butyl(meth)acrylate, 2-hydroxyethyl(meth)acrylate, 2-hydroxybutyl(meth)acrylate, benzyl(meth)acrylate, cyclohexyl(meth)acrylate, phenyl(meth)acrylate, and the like; unsaturated carboxylic acid amino alkyl ester compounds such as 2-aminoethyl(meth)acrylate, 2-dimethylaminoethyl(meth)

acrylate, and the like; carboxylic acid vinyl ester compounds such as vinyl acetate, vinyl benzoate, and the like; unsaturated carboxylic acid glycidyl ester compounds such as glycidyl (meth)acrylate, and the like; vinyl cyanide compounds such as (meth)acrylonitrile and the like; unsaturated amide compounds such as (meth)acrylamide, and the like; and the like, and may be used singularly or as a mixture of two or more.

Specific examples of the acrylic-based resin may include without limitation an acrylic acid/benzylmethacrylate copolymer, a methacrylic acid/benzylmethacrylate copolymer, a methacrylic acid/benzyl methacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like. These may be used singularly or as a mixture of two or more.

The alkali soluble resin may have a weight average molecular weight of about 3,000 g/mol to about 150,000 g/mol, for example about 5,000 g/mol to about 50,000 g/mol, and as another example about 20,000 g/mol to about 30,000 g/mol. When the alkali soluble resin has a weight average molecular weight within the above range, the photosensitive resin composition for a color filter can have good physical and chemical properties, appropriate viscosity, and/or close contacting (adhesive) properties with a substrate during manufacture of a color filter.

The alkali soluble resin may have an acid value of about 15 mgKOH/g to about 60 mgKOH/g, for example about 20 mgKOH/g to about 50 mgKOH/g. When the alkali soluble resin has an acid value within the above range, a pixel pattern may have excellent resolution.

The photosensitive resin composition may include the alkali soluble resin in an amount of about 1 wt % to about 40 wt %, for example about 1 wt % to about 20 wt %, based on the total amount (total weight, 100 wt %) of the photosensitive resin composition for a color filter. In some embodiments, the photosensitive resin composition may include the alkali soluble resin in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 wt %. Further, according to some embodiments of the present invention, the amount of the alkali soluble resin can be in a range from about any of the foregoing amounts to about any other of the foregoing amounts.

When the alkali soluble resin is included in an amount within the above range, developability may be improved and excellent surface smoothness may be improved due to improved cross-linking during the manufacture of a color filter.

The photopolymerizable compound may be a mono-functional and/or multi-functional ester of (meth)acrylic acid including at least one ethylenic unsaturated double bond.

The photopolymerizable compound has the ethylenic unsaturated double bond and thus may cause sufficient polymerization during exposure in a pattern-forming process and form a pattern having excellent heat resistance, light resistance, and chemical resistance.

Examples of the photopolymerizable compound may include without limitation ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether(meth)acrylate, trimethylol propane tri(meth)acrylate, tris(meth)acryloyloxyethyl phosphate, novolac epoxy(meth)acrylate, and the like, and combinations thereof.

Commercially available examples of the photopolymerizable compound include the following. Examples of the monofunctional ester of (meth)acrylic acid may include without limitation Aronix M-101®, M-111® and/or M-114® (Toagosei Chemistry Industry Co., Ltd.); KAYARAD TC-110S® and/or TC-120S® (Nippon Kayaku Co., Ltd.); V-158® and/or V-2311® (Osaka Organic Chemical Ind., Ltd.), and the like. Examples of a difunctional ester of (meth)acrylic acid may include without limitation Aronix M-210®, M-240® and/or M-6200® (Toagosei Chemistry Industry Co., Ltd.), KAYARAD HDDA®, HX-220® and/or R-604® (Nippon Kayaku Co., Ltd.), V-260®, V-312® and/or V-335 HP® (Osaka Organic Chemical Ind., Ltd.), and the like. Examples of a tri-functional ester of (meth)acrylic acid may include without limitation Aronix M-309®, M-400®, M-405®, M-450®, M-7100®, M-8030® and/or M-8060® (Toagosei Chemistry Industry Co., Ltd.), KAYARAD TMPTA®, DPCA-20®, DPCA-30®, DPCA-60® and/or DPCA-120® (Nippon Kayaku Co., Ltd.), V-295®, V-300®, V-360®, V-GPT®, V-3PA® and/or V-400® (Osaka Yuki Kayaku Kogyo Co. Ltd.), and the like. These may be used singularly or as a mixture of two or more.

The photopolymerizable compound may be treated with acid anhydride to improve developability.

The photosensitive resin composition may include the photopolymerizable compound in an amount of about 1 wt % to about 15 wt %, for example about 5 wt % to about 10 wt %, based on the total amount (total weight, 100 wt %) of the photosensitive resin composition. In some embodiments, the photosensitive resin composition may include the photopolymerizable compound in an amount of about 1, 2, 3, 4, 5, 6, 7, 8, 9, 10, 11, 12, 13, 14, or 15 wt %. Further, according to some embodiments of the present invention, the amount of the photopolymerizable compound can be in a range from about any of the foregoing amounts to about any other of the foregoing amounts.

When the photopolymerizable compound is included in an amount within the above range, the photopolymerizable compound can be sufficiently cured during exposure in a pattern-forming process and can have excellent reliability, and developability for alkali developing solution may be improved.

The photopolymerization initiator can be any generally-used initiator for a photosensitive resin composition, for example an acetophenone-based compound, a benzophenone-based compound, a thioxanthone-based compound, a benzoin-based compound, an oxime-based compound, or a combination thereof.

Examples of the acetophenone-based compound may include without limitation 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like, and combinations thereof.

Examples of the benzophenone-based compound may include without limitation benzophenone, benzoyl benzoate, benzoyl methyl benzoate ester, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like, and combinations thereof.

Examples of the thioxanthone-based compound may include without limitation thioxanthone, 2-methylthioxanthone, isopropyl thioxanthone, 2,4-diethyl thioxanthone, 2,4-diisopropyl thioxanthone, 2-chlorothioxanthone, and the like, and combinations thereof.

Examples of the benzoin-based compound may include without limitation benzoin, benzoin methyl ether, benzoin ethyl ether, benzoin isopropyl ether, benzoin isobutyl ether, benzyldimethyl ketal, and the like, and combinations thereof.

Examples of the triazine-based compound may include without limitation 2,4,6-trichloro-s-triazine, 2-phenyl-4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl-4,6-bis(trichloro methyl)-s-triazine, bis(trichloromethyl)-6-styryl-s-triazine, 2-(naphtho1-yl)-4,6-bis(trichloromethyl)-s-triazine, 2-(4-methoxynaphtho1-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like, and combinations thereof.

Examples of the oxime-based compound may include without limitation O-acyloxime-based compounds, 2-(o-benzoyloxime)-1-[4-(phenylthio)phenyl]-1,2-octandione, 1-(o-acetyloxime)-1-[9-ethyl-6-(2-methylbenzoyl)-9H-carbazol-3-yl]ethanone, 0-ethoxycarbonyl-α-oxyamino-1-phenylpropan-1-one and the like, and combinations thereof. Examples of the O-acyloxime-based compound may include without limitation 1,2-octandione, 2-dimethylamino-2-(4-methylbenzyl)-1-(4-morpholin-4-yl-phenyl)butan-1-one, 1-(4-phenylsulfanyl phenyl)-butane-1,2-dione 2-oxime-O-benzoate, 1-(4-phenylsulfanyl phenyl)-octane-1,2-dione2-oxime-O-benzoate, 1-(4-phenylsulfanyl phenyl)-octan-1-one oxime-O-acetate and 1-(4-phenylsulfanyl phenyl)butan-1-oneoxime-O-acetate, and the like, and combinations thereof.

The photopolymerization initiator may further include one or more of a carbazole-based compound, a diketone-based compound, a sulfonium borate-based compound, a diazo-based compound, an imidazole-based compound, a biimidazole-based compound, and the like instead of or in addition to one of the above compounds.

The photopolymerization initiator may be used with a photosensitizer capable of causing a chemical reaction by absorbing light and becoming excited and then, transferring its energy.

Examples of the photosensitizer may include without limitation tetraethylene glycol bis-3-mercapto propionate, pentaerythritol tetrakis-3-mercapto propionate, dipentaerythritol tetrakis-3-mercapto propionate, and the like, and combinations thereof.

The photosensitive resin composition may include the photopolymerization initiator in an amount of about 0.01 wt % to about 10 wt %, for example about 0.1 wt % to about 5 wt %, based on the total amount (total weight, 100 wt %) of the photosensitive resin composition. In some embodiments, the photosensitive resin composition may include the photopolymerization initiator in an amount of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 wt %. Further, according to some embodiments of the present invention, the amount of the photopolymerization initiator can be in a range from about any of the foregoing amounts to about any other of the foregoing amounts.

When the photopolymerization initiator is included in an amount within the above range, excellent reliability may be secured due to sufficiently curing during exposure in a pattern-forming process, a pattern may have excellent resolution and close-contacting properties as well as excellent heat resistance, light resistance, and chemical resistance, and transmittance may be prevented from deterioration due to a non-reaction initiator.

The solvent is a material having compatibility with the compound or the mixture, the alkali soluble resin, the photopolymerizable compound, and the photopolymerization initiator but not reacting therewith.

Examples of the solvent may include without limitation alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such as 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like; and combinations thereof. Additionally, high boiling point solvent such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like may be also used. The solvents may be used singularly or as a mixture of two or more.

Considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; and/or propylene glycol alkylether acetates such as propylene glycol methylether acetate, propylene glycol propylether acetate and the like may be used.

The photosensitive resin composition may include the solvent in a balance amount, for example about 40 wt % to about 90 wt % based on the total amount (total weight, 100 wt %) of the photosensitive resin composition. In some embodiments, the photosensitive resin composition may include the solvent in an amount of about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %. Further, according to some embodiments of the present invention, the amount of the solvent can be in a range from about any of the foregoing amounts to about any other of the foregoing amounts.

When the solvent is included in an amount within the above range, the photosensitive resin composition may have an appropriate viscosity resulting in improvement of coating characteristics of a color filter.

The photosensitive resin composition according to another embodiment may further include an epoxy compound in order to improve a close contacting property with a substrate.

Examples of the epoxy compound may include without limitation phenol novolac epoxy compounds, tetramethyl biphenyl epoxy compounds, bisphenol A epoxy compounds, alicyclic epoxy compounds, and the like, and combinations thereof.

The epoxy compound may be included in an amount of about 0.01 parts by weight to about 20 parts by weight, for example about 0.1 parts by weight to about 10 parts by weight, based on about 100 parts by weight of the photosensitive resin composition. When the epoxy compound is included in an amount within the above range, close contacting properties, storage capability, and the like may be improved.

The photosensitive resin composition may further include a silane coupling agent having a reactive substituent such as a carboxyl group, a methacryloyl group, an isocyanate group, an epoxy group, and the like in order to improve adherence to a substrate.

Examples of the silane coupling agent include without limitation trimethoxysilyl benzoic acid, γ-methacryl oxypropyl trimethoxysilane, vinyl triacetoxysilane, vinyl trimethoxysilane, γ-isocyanate propyl triethoxysilane, γ-glycidoxy propyl trimethoxysilane, β-(3,4-epoxycyclohexyl) ethyltrimethoxysilane, and the like. These may be used singularly or in a mixture of two or more.

The silane coupling agent may be included in an amount of about 0.01 parts by weight to about 10 parts by weight based on about 100 parts by weight of the photosensitive resin composition. When the silane coupling agent is included in an amount within the above range, close contacting properties, storage properties, and the like can be improved.

The photosensitive resin composition may further include a surfactant in order to improve coating properties and inhibit generation of spots.

Examples of the surfactant may include without limitation a fluorene-based surfactant, for example, BM-1000® and/or BM-1100® (BM Chemie Inc.); MEGAFACE F 142D®, F 172®, F 173®, and/or F 183® (Dainippon Ink Kagaku Kogyo Co., Ltd.); FULORAD FC-135®, FULORAD FC-170C®, FULORAD FC-430®, and/or FULORAD FC-431® (Sumitomo 3M Co., Ltd.); SURFLON S-112®, SURFLON S-113®, SURFLON S-131®, SURFLON S-141®, and/or SURFLON S-145® (ASAHI Glass Co., Ltd.); and SH-28PA®, SH-190®, SH-193®, SZ-6032®, and/or SF-8428® (Toray Silicone Co., Ltd.), and the like, and combinations thereof.

The surfactant may be included in an amount of about 0.001 to about 5 parts by weight based on about 100 parts by weight of the photosensitive resin composition. When the surfactant is included in an amount within the above range, coating uniformity may be ensured, stains may not be generated, and wetting properties for a glass substrate can be improved.

The photosensitive resin composition may further include one or more other additives such as an antioxidant, a stabilizer, and the like, and combinations thereof in a predetermined amount.

According to another embodiment of the present invention, a color filter manufactured using the photosensitive resin composition is provided.

An exemplary pattern-forming process for making the color filter is as follows.

The process includes coating the positive photosensitive resin composition on a support substrate using a method such as spin coating, slit coating, inkjet printing, and the like; drying the coated positive photosensitive resin composition to form a photosensitive resin composition film; exposing the positive photosensitive resin composition film to light; developing the exposed positive photosensitive resin composition film in an alkali aqueous solution to obtain a photosensitive resin film; and heat-treating the photosensitive resin film. Conditions for the patterning process are well known in the art and will not be illustrated in detail in the present specification.

Hereinafter, the present invention is illustrated in more detail with reference to the following examples and comparative examples. However, the following examples and comparative examples are provided for the purpose of illustration and the present invention is not limited thereto.

Synthesis

Synthesis Example 1

Synthesis of Compound Represented by Chemical Formula 3-1

(1) 3,4,5,6-tetrachlorophthalonitrile (5 g), 2-phenylphenol (3.201 g), $K_2CO_3$ (3.898 g) and acetonitrile (50 ml) are put in a 100 ml flask and then heated and refluxed. When the reaction is complete, the resultant is filtered with tetrahydrofuran (THF) to obtain a solid, the solid is added to a small amount of dichloromethane and dissolved therein, and hexane is added thereto, obtaining a crystallized solid (4-(biphenyl-2-yloxy)-3,5,6-trichlorophthalonitrile). Herein, the obtained solid is washed several times, filtered and vacuum-dried.

(2) The solid (4-(biphenyl-2-yloxy)-3,5,6-trichlorophthalonitrile) (1.0 g), 3,4,5,6-tetrachlorophthalonitrile (0.22 g), 1,8-diazabicycloundec-7-ene (1.0 g) and 1-pentenol (10 mL) are put in a 100 mL flask and then heated and dissolved. Then, zinc acetate (0.15 g) is added thereto, and the mixture is heated and refluxed. When the reaction is complete, a solvent is removed therefrom, and the remnant is purified through column chromatography. Subsequently, dichloromethane is moderately added to the obtained solid to dissolve it, and hexane is added thereto to perform crystallization. Herein, a solid obtained therefrom is filtered and vacuum-dried, obtaining a compound represented by the following Chemical Formula 3-1.

[Chemical Formula 3-1]

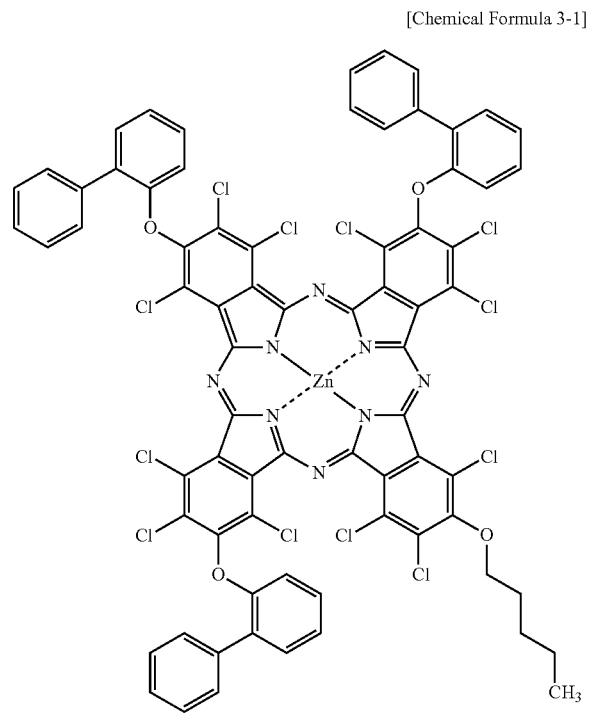

Maldi-tof MS 1581.90 m/z

Synthesis Example 2

Synthesis of Compound Represented by Chemical Formula 4-1

The solid (4-(biphenyl-2-yloxy)-3,5,6-trichlorophthalonitrile) (1.0 g), 3,4,5,6-tetrachlorophthalonitrile (0.67 g), 1,8-diazabicycloundec-7-ene (1.5 g) and 1-pentenol (15 mL) are put in a 100 mL flask and then, heated and dissolved. Then, zinc acetate (0.23 g) is added thereto, and the mixture is heated and refluxed. When the reaction is complete, a solvent is removed therefrom, and the remnant is purified through column chromatography. Then, dichloromethane is moderately added to the obtained solid to dissolve it, and hexane is added thereto to perform crystallization. Herein, the obtained solid is filtered and vacuum-dried, obtaining a compound represented by the following Chemical Formula 4-1.

[Chemical Formula 4-1]

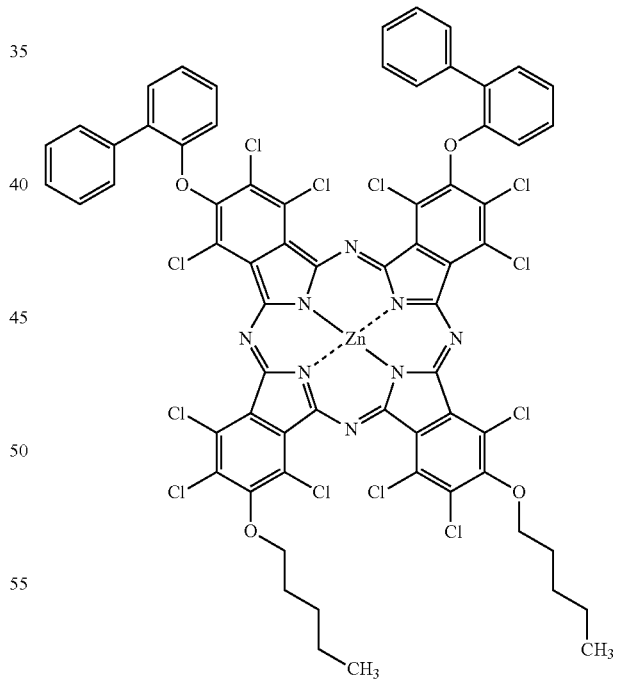

Maldi-tof MS 1499.93 m/z

Synthesis Example 3

Synthesis of Compound Represented by Chemical Formula 6-1

The solid (4-(biphenyl-2-yloxy)-3,5,6-trichlorophthalonitrile) (1.0 g), 3,4,5,6-tetrachlorophthalonitrile (2.0 g), 1,8-diazabicycloundec-7-ene (3.0 g) and 1-pentenol (30 mL) are put in a 100 mL flask and then heated and dissolved. Then, zinc acetate (0.46 g) is added thereto, and the mixture is heated and refluxed. When the reaction is complete, a solvent is removed therefrom, and the remnant is purified through column chromatography. Then, dichloromethane is moderately added to the obtained solid to dissolve it, and hexane is added thereto to perform crystallization. Herein, the obtained solid is filtered and vacuum-dried, obtaining a compound represented by the following Chemical Formula 6-1.

[Chemical Formula 6-1]

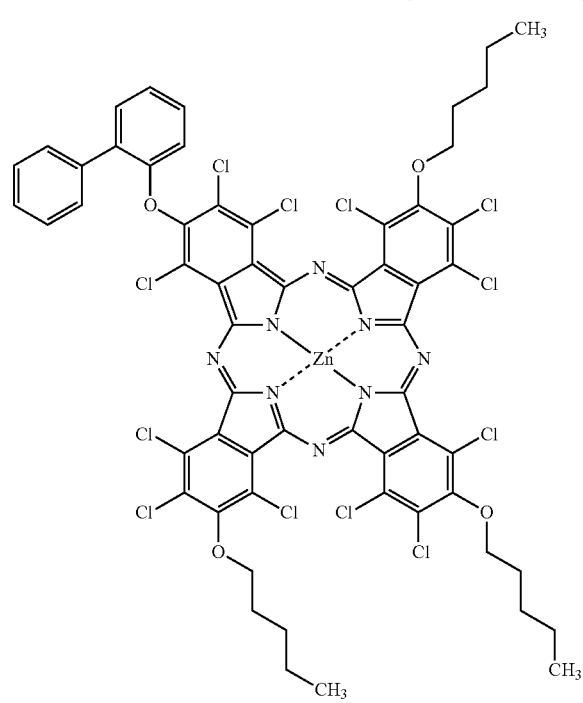

Maldi-tof MS 1417.93 m/z

Comparison Synthesis Example 1

Synthesis of Compound Represented by Chemical Formula 7

The solid (4-(biphenyl-2-yloxy)-3,5,6-trichlorophthalonitrile) (1.0 g), 1,8-diazabicycloundec-7-ene (0.7 g) and 1-pentenol (15 mL) are put in a 100 mL flask and then heated to dissolve the 4-(biphenyl-2-yloxy)-3,5,6-trichlorophthalonitrile. Then, zinc acetate (0.115 g) is added thereto, and the mixture is heated and refluxed. When the reaction is complete, a solvent is removed therefrom, and a remnant is purified through column chromatography. Then, dichloromethane is moderately added to the obtained solid to dissolve it, and hexane is added thereto to perform crystallization. Herein, the obtained solid is filtered and vacuum-dried, obtaining a compound represented by the following Chemical Formula 7.

[Chemical Formula 7]

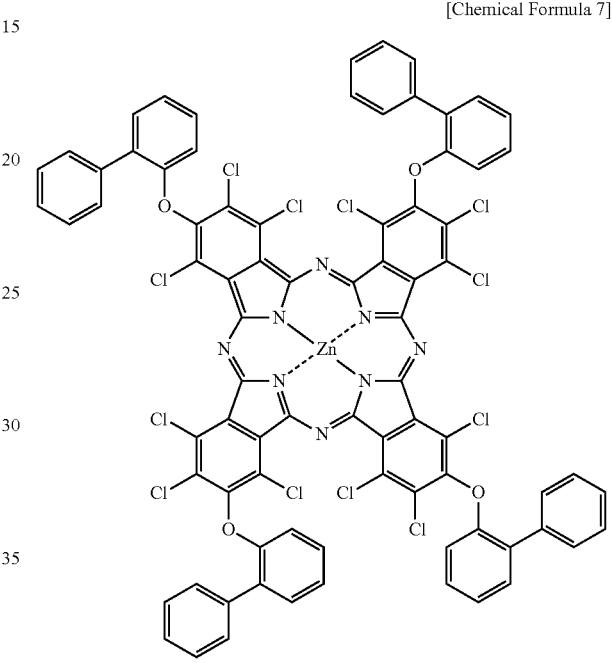

Maldi-tof MS 1664.80 m/z

Comparison Synthesis Example 2

Synthesis of Compound Represented by Chemical Formula 8

3,4,6-trichloro-5-(pentyloxy)phthalonitrile (1.0 g), 1,8-diazabicycloundec-7-ene (0.96 g) and 1-pentenol (20 mL) are put in a 100 mL flask and then heated to dissolve 3,4,6-trichloro-5-(pentyloxy)phthalonitrile. Then, zinc acetate (0.14 g) is added thereto, and the mixture is heated and refluxed. When the reaction is complete, a solvent is removed therefrom, and the remnant is purified through column chromatography. Then, dichloromethane is moderately added to the obtained solid to dissolve it, and hexane is added thereto to perform crystallization. Herein, the obtained solid is filtered and vacuum-dried, obtaining a compound represented by the following Chemical Formula 8.

[Chemical Formula 8]

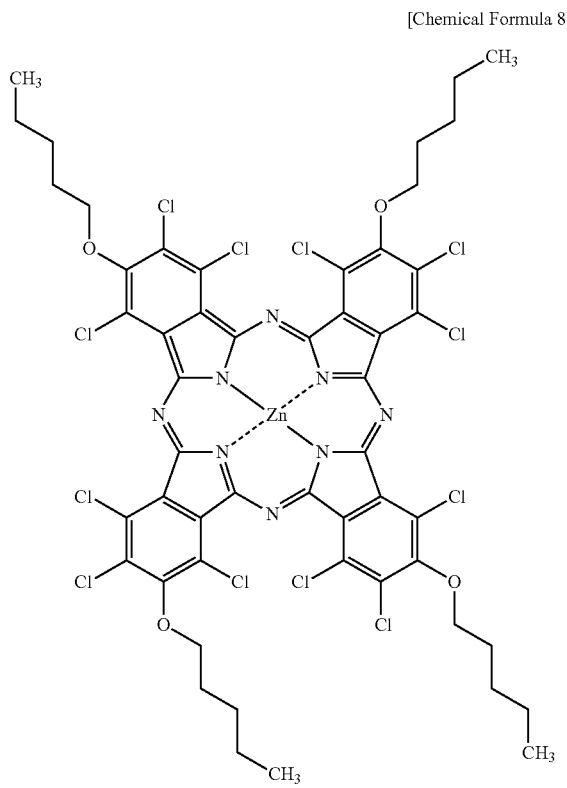

Maldi-tof MS: 1335.70 m/z

Synthesis of Photosensitive Resin Composition

Example 1

A photosensitive resin composition according to Example 1 is to manufactured by mixing the following components in a composition provided in the following Table 1.

Specifically, a photopolymerization initiator is dissolved in a solvent, the solution is agitated at room temperature for 2 hours, an alkali soluble resin and a photopolymerizable compound are added thereto, and the mixture is agitated at room temperature for 2 hours. Then, the compound (represented by Chemical Formula 3-1) according to Synthesis Example 1 and a pigment (in a pigment dispersion state) as a colorant are added to the reactant, and the mixture is agitated at room temperature for one hour. Then, the product is three times filtered to remove impurities, preparing a photosensitive resin composition.

TABLE 1

| Composition materials | | | Amounts |
|---|---|---|---|
| Colorant | Dye | Compound of Synthesis Example 1 | 5.0 |
| | Pigment | Pigment Y138 | 15.0 |
| Alkali soluble resin | | (A) / (B) = 15/85 (w/w), molecular weight (Mw) = 22,000 g/mol (A): methacrylic acid (B): benzylmethacrylate | 3.5 |
| Photopolymerizable compound | | Dipentaerythritolhexaacrylate (DPHA) | 8.0 |
| Photopolymerization initiator | | 1,2-octandione 2-dimethylamino-2-(4-methyl-benzyl)-1-(4-morpholine -4-yl-phenyl)-butan-1-one | 1.0 0.5 |

TABLE 1-continued

| Composition materials | | Amounts |
|---|---|---|
| Solvent | Cyclohexanone | 37.0 |
| | PGMEA (Propylene Glycol Monomethyl Ether Acetate) | 30.0 |
| | Sum (Total) | 100.0 |

(unit: wt %)

Example 2

A photosensitive resin composition is prepared according to the same method as Example 1 except for using the compound of Synthesis Example 2 (represented by Chemical Formula 4-1) instead of the compound of Synthesis Example 1 (represented by Chemical Formula 3-1).

Example 3

A photosensitive resin composition is prepared according to the same method as Example 1 except for using the compound of Synthesis Example 3 (represented by Chemical Formula 6-1) instead of the compound of Synthesis Example 1 (represented by Chemical Formula 3-1).

Comparative Example 1

A photosensitive resin composition is prepared according to the same method as Example 1 except for using the compound of Comparison Synthesis Example 1 (represented by Chemical Formula 7) instead of the compound of Synthesis Example 1 (represented by Chemical Formula 3-1).

Comparative Example 2

A photosensitive resin composition is prepared according to the same method as Example 1 except for using the compound of Comparison Synthesis Example 3 (represented by Chemical Formula 8) instead of the compound of Synthesis Example 1 (represented by Chemical Formula 3-1).

Evaluation: Measurement of Color Coordinate, Luminance and Contrast Ratio

The photosensitive resin compositions according to Examples 1 to 3 and Comparative Examples 1 and 2 are respectively coated to be 1 μm to 3 μm thick on a 1 mm-thick degreased glass substrate and dried on a 90° C. hot plate for 2 minutes, obtaining each film. Subsequently, the film is exposed to light by using a high pressure mercury lamp with a main wavelength of 365 nm. The film is dried in a 200° C. forced convection drying furnace for 5 minutes. As for a pixel layer including the film, a color coordinate (x, y), luminance (Y) and a contrast ratio are measured by using a spectrophotometer (MCPD3000, Otsuka Electronics Inc.), and the results are provided in the following Table 2.

TABLE 2

| | Color coordinate (x, y) | Luminance (Y) | Contrast ratio |
|---|---|---|---|
| Example 1 | 0.281, 0.579 | 62.9 | 15,600 |
| Example 2 | 0.282, 0.578 | 63.5 | 15,200 |
| Example 3 | 0.275, 0.577 | 63.4 | 15,700 |
| Comparative Example 1 | 0.279, 0.579 | 61.2 | 14,800 |
| Comparative Example 2 | 0.276, 0.579 | 59.6 | 14,300 |

Referring to Table 2, the photosensitive resin compositions of Examples 1 to 3 including a compound according to one embodiment of the present invention as a dye exhibit excellent color characteristics compared with the photosensitive resin compositions of Comparative Examples 1 and 2 not including the compound.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

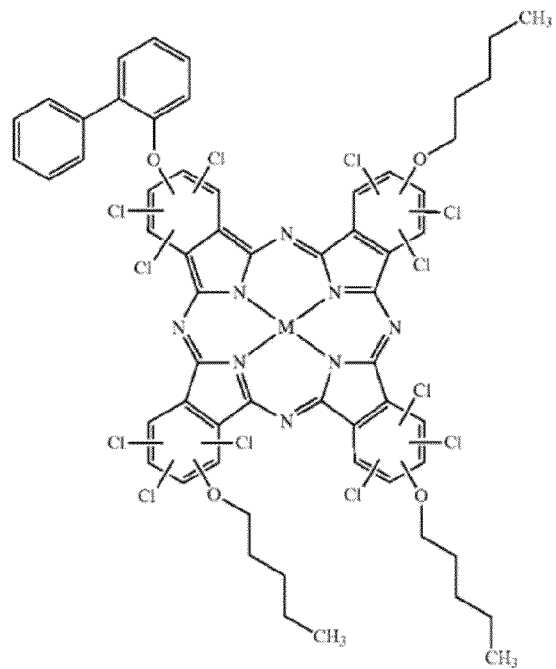 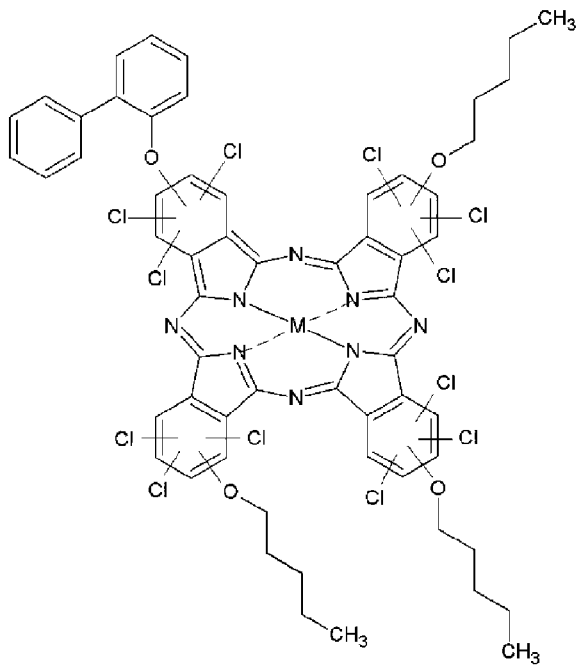

What is claimed is:

1. A compound represented by the following Chemical Formula 1:

[Chemical Formula 1]

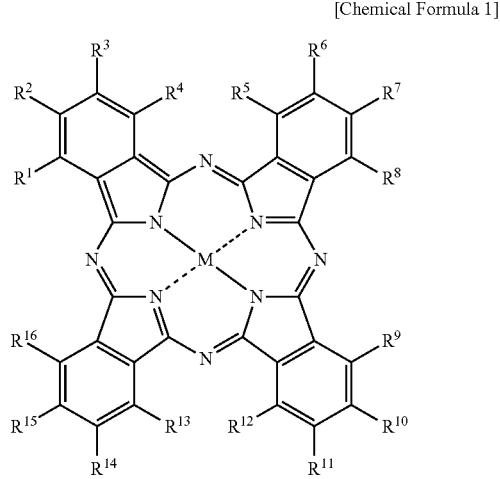

wherein, in the above Chemical Formula 1,

M is Cu, Zn, Co, or Mo, $R^1$ to $R^{16}$ are the same or different and are each independently hydrogen, halogen, substituted or unsubstituted C1 to C20 alkyl, substituted or unsubstituted C1 to C20 alkoxy, substituted or unsubstituted C6 to C20 aryl, or substituted or unsubstituted C6 to C20 aryloxy, wherein at least one of $R^1$ to $R^{16}$ is substituted or unsubstituted C1 to C20 alkoxy, and wherein at least one of $R^1$ to $R^{16}$ is substituted or unsubstituted C6 to C20 aryloxy represented by the following Chemical Formula 2:

[Chemical Formula 2]

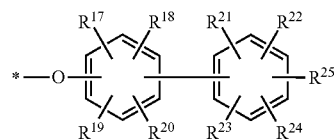

wherein, in the above Chemical Formula 2, $R^{17}$ to $R^{25}$ are the same or different and are each independently hydrogen, halogen, or substituted or unsubstituted C1 to C8 alkyl.

2. The compound of claim 1, wherein C1 to C20 alkoxy is methoxy, ethoxy, propoxy, butoxy, pentyloxy, hexyloxy, heptyloxy, octyloxy, nonyloxy, decyloxy, or a combination thereof.

3. The compound of claim 1, wherein at least one of $R^1$ to $R^4$ is substituted or unsubstituted C6 to C20 aryloxy,
   at least one of $R^5$ to $R^8$ is substituted or unsubstituted C6 to C20 aryloxy,
   at least one of $R^9$ to $R^{12}$ is substituted or unsubstituted C6 to C20 aryloxy, and
   at least one of $R^{13}$ to $R^{16}$ is substituted or unsubstituted C1 to C20 alkoxy.

4. The compound of claim 1, wherein at least one of $R^1$ to $R^4$ is substituted or unsubstituted C6 to C20 aryloxy,
   at least one of $R^5$ to $R^8$ is substituted or unsubstituted C1 to C20 alkoxy,
   at least one of $R^9$ to $R^{12}$ is substituted or unsubstituted C1 to C20 alkoxy, and
   at least one of $R^{13}$ to $R^{16}$ is substituted or unsubstituted C1 to C20 alkoxy.

5. The compound of claim 1, wherein at least one of $R^1$ to $R^4$ is substituted or unsubstituted C6 to C20 aryloxy,
   at least one of $R^5$ to $R^8$ is substituted or unsubstituted C1 to C20 alkoxy,
   at least one of $R^9$ to $R^{12}$ is substituted or unsubstituted C6 to C20 aryloxy, and
   at least one of $R^{13}$ to $R^{16}$ is substituted or unsubstituted C1 to C20 alkoxy.

6. The compound of claim 1, wherein at least one of $R^1$ to $R^4$ is substituted or unsubstituted C6 to C20 aryloxy,
   at least one of $R^5$ to $R^8$ is substituted or unsubstituted C6 to C20 aryloxy,
   at least one of $R^9$ to $R^{12}$ is substituted or unsubstituted C1 to C20 alkoxy, and
   at least one of $R^{13}$ to $R^{16}$ is substituted or unsubstituted C1 to C20 alkoxy.

7. The compound of claim 1, wherein the compound is represented by one or more of the following Chemical Formulae 3 to 6:

[Chemical Formula 3]
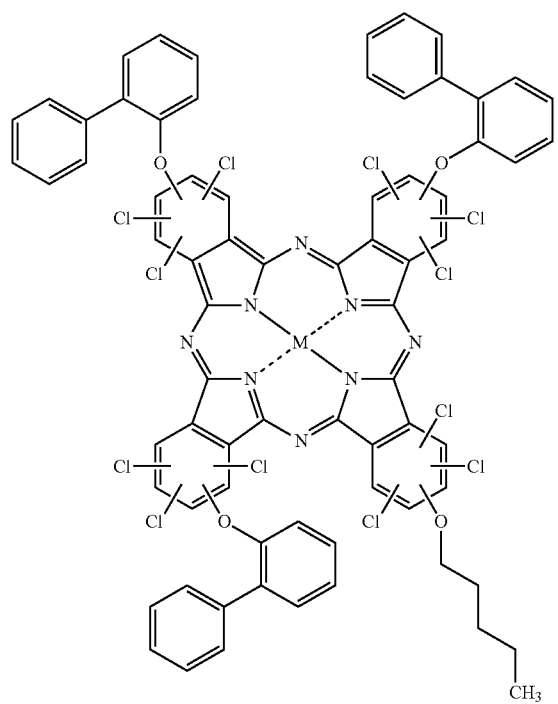
[Chemical Formula 4]
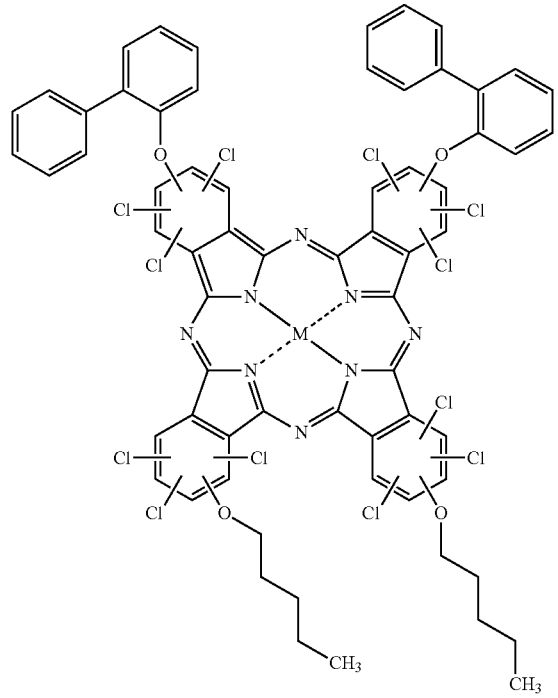
[Chemical Formula 5]
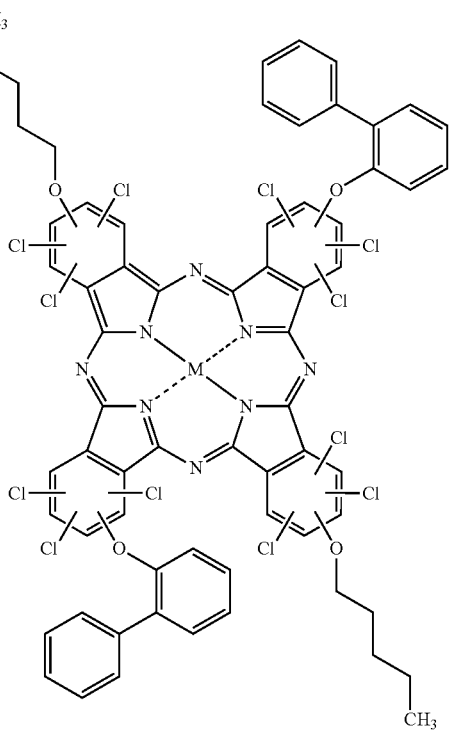
[Chemical Formula 6]
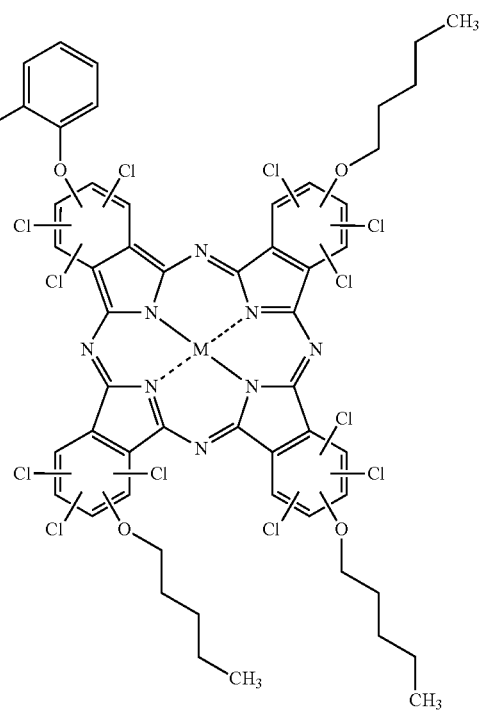
wherein, in the above Chemical Formulae 3 to 6, M is Cu, Zn, Co, or Mo.
8. The compound of claim 1, wherein the compound is a green dye.
9. A photosensitive resin composition comprising the compound of claim 1.

10. A color filter manufactured using the photosensitive resin composition of claim 9.

11. A mixture of at least two or more compounds of compounds represented by the below Chemical Formulae 3 to 6:

[Chemical Formula 3]

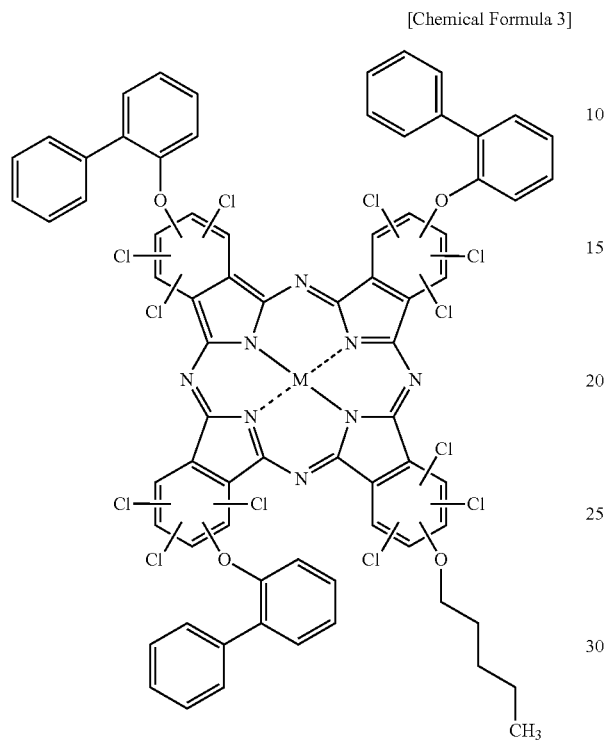

[Chemical Formula 4]

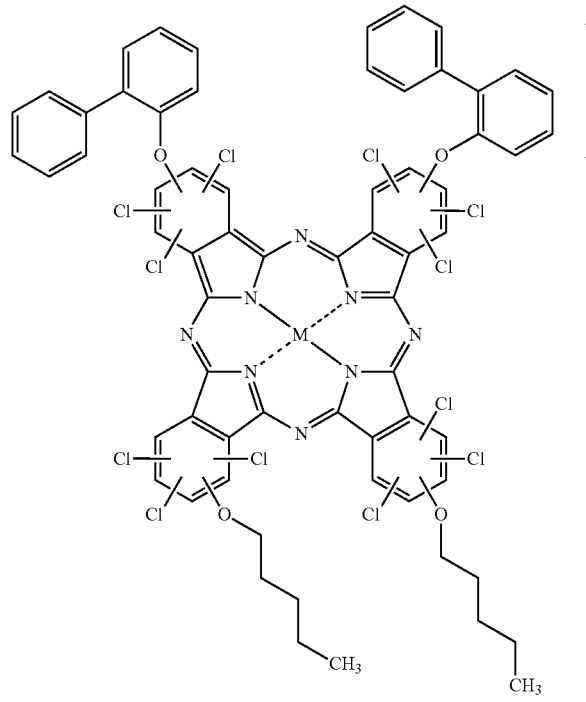

[Chemical Formula 5]

[Chemical Formula 6]

wherein, in the above Chemical Formulae 3 to 6,
M is Cu, Zn, Co, or Mo.

12. A photosensitive resin composition comprising the mixture of claim 11.

13. A color filter manufactured using the photosensitive resin composition of claim 12.

* * * * *

UNITED STATES PATENT AND TRADEMARK OFFICE
CERTIFICATE OF CORRECTION

PATENT NO. : 9,242,990 B2
APPLICATION NO. : 14/528125
DATED : January 26, 2016
INVENTOR(S) : Myoung-Youp Shin et al.

It is certified that error appears in the above-identified patent and that said Letters Patent is hereby corrected as shown below:

On the Title Page

In the Abstract

Chemical Formula 1 is depicted as:        and should be depicted as:

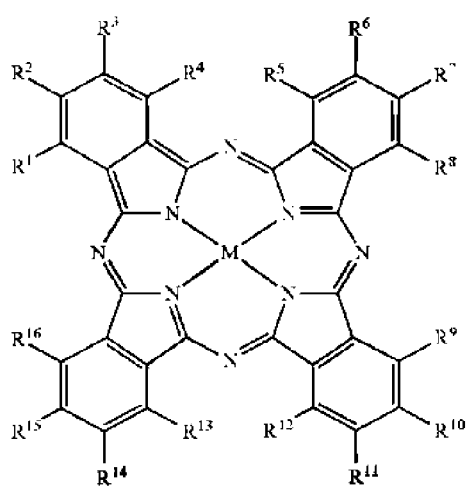   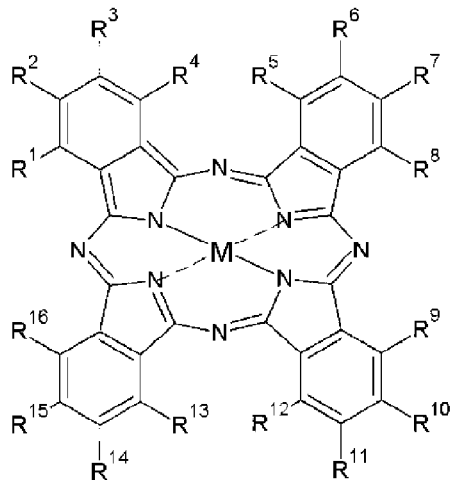

Signed and Sealed this
Thirty-first Day of May, 2016

Michelle K. Lee
*Director of the United States Patent and Trademark Office*

CERTIFICATE OF CORRECTION (continued)
U.S. Pat. No. 9,242,990 B2

In the Specification

Column 1, Chemical Formula 1 is depicted as:  and should be depicted as:

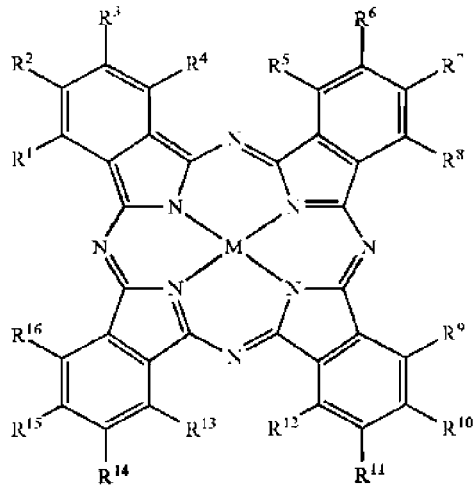 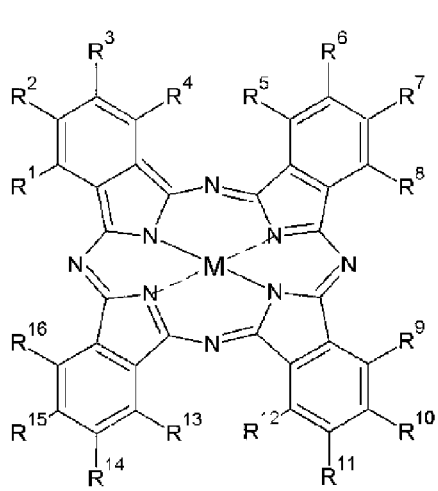

Column 3, Chemical Formula 3 is depicted as:  and should be depicted as:

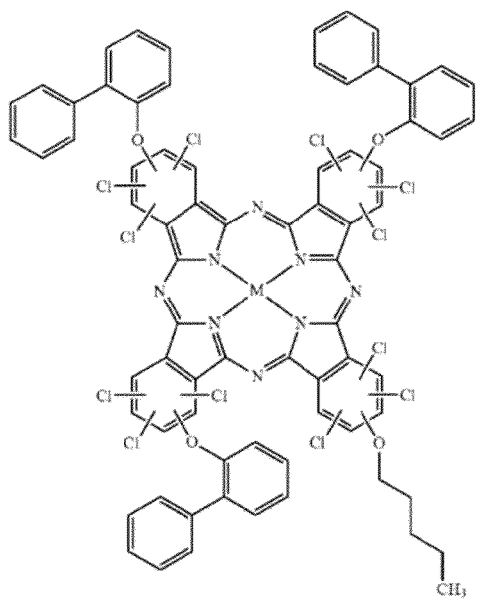 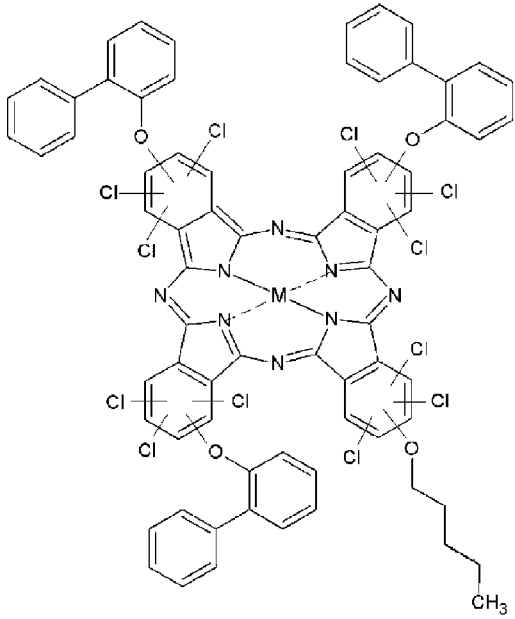

CERTIFICATE OF CORRECTION (continued)

Page 3 of 6

U.S. Pat. No. 9,242,990 B2

In the Specification

Column 3, Chemical Formula 4 is depicted as:

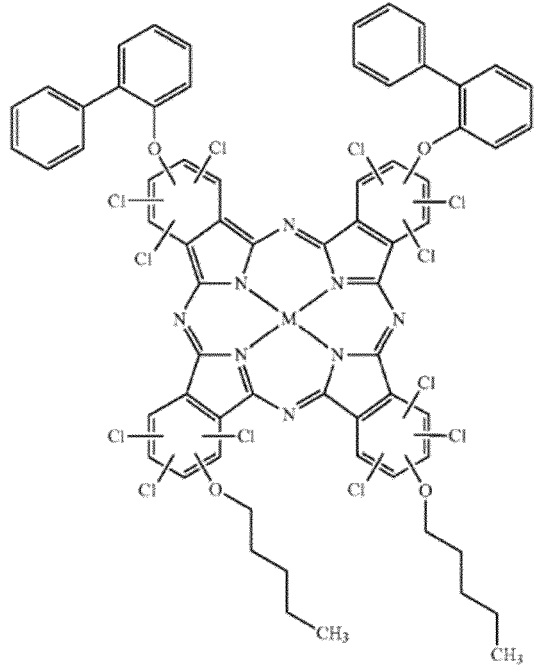

and should be depicted as:

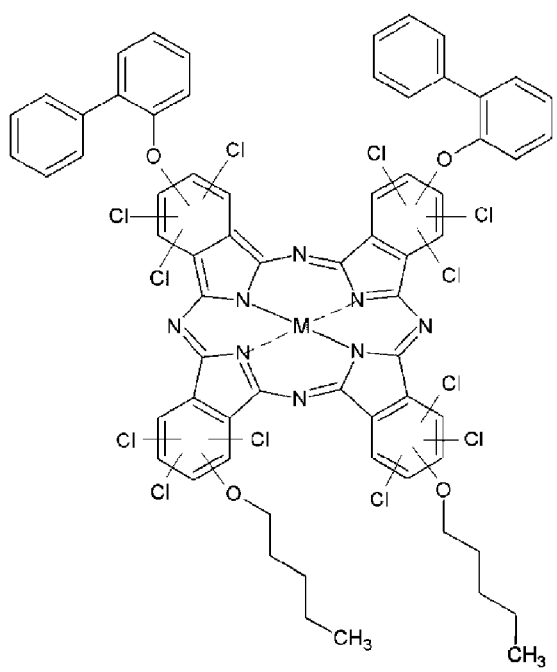

Column 4, Chemical Formula 5 is depicted as:

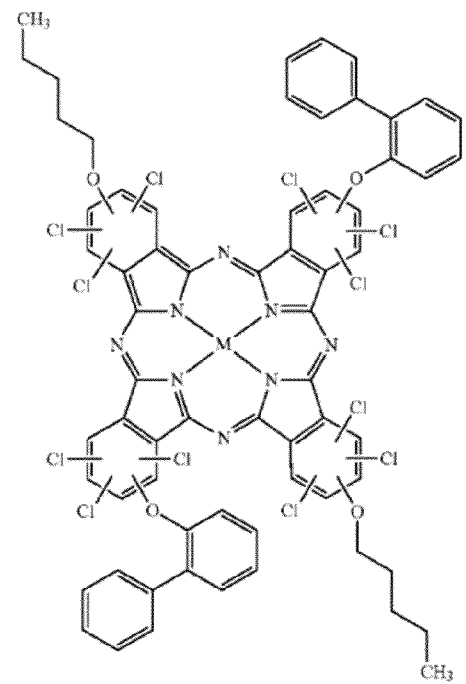

and should be depicted as:

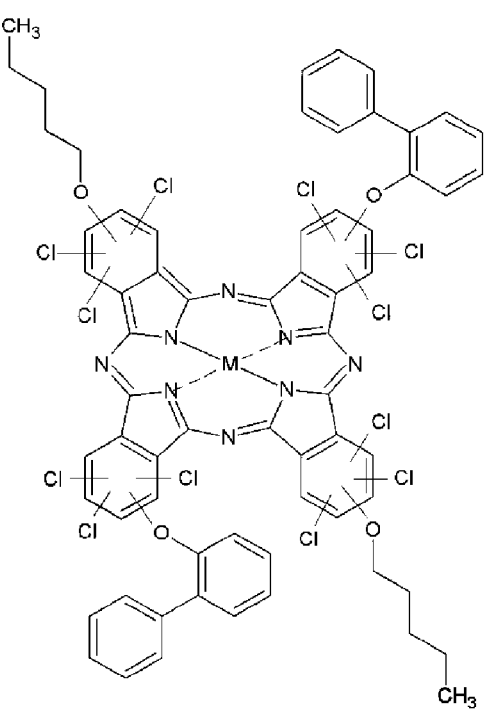

CERTIFICATE OF CORRECTION (continued)
U.S. Pat. No. 9,242,990 B2

In the Specification

Column 4, Chemical Formula 6 is depicted as:

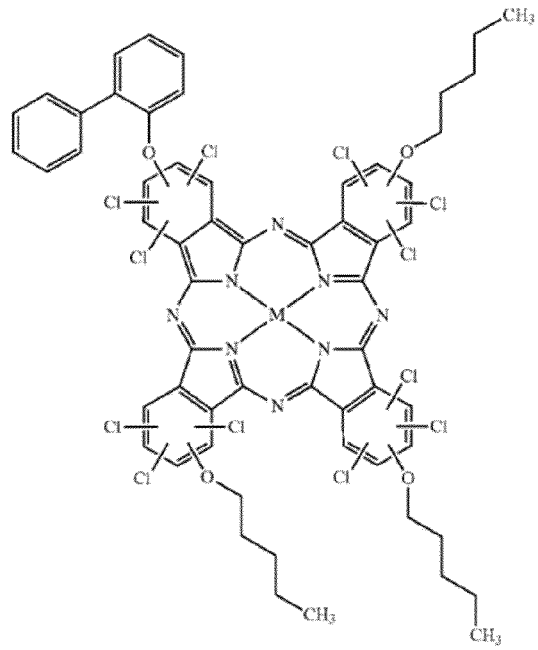

and should be depicted as:

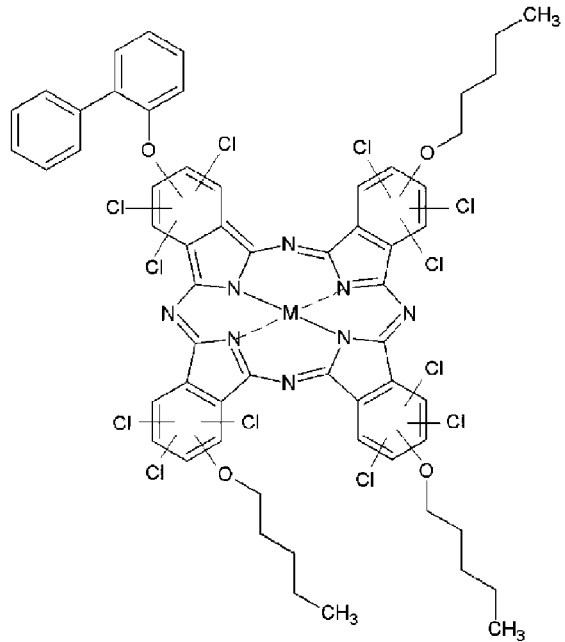

Column 6, Chemical Formula 1 is depicted as:

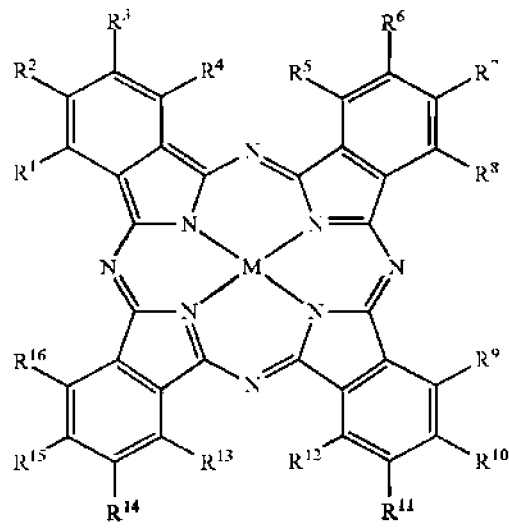

and should be depicted as:

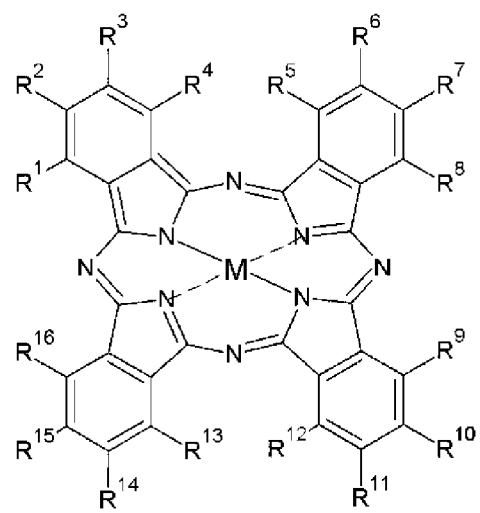

CERTIFICATE OF CORRECTION (continued)

In the Specification

Column 8, Chemical Formula 3 is depicted as:

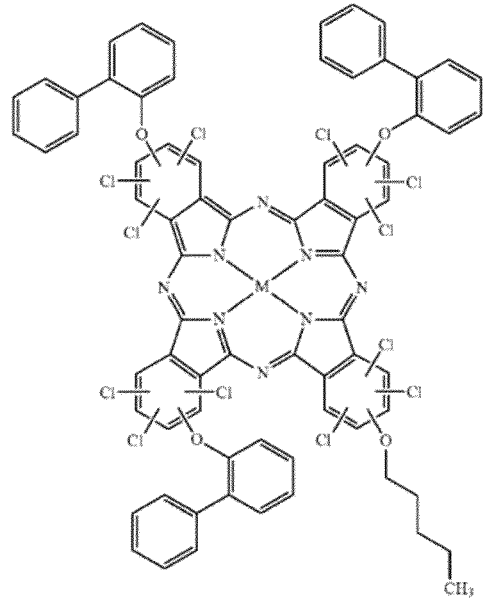

and should be depicted as:

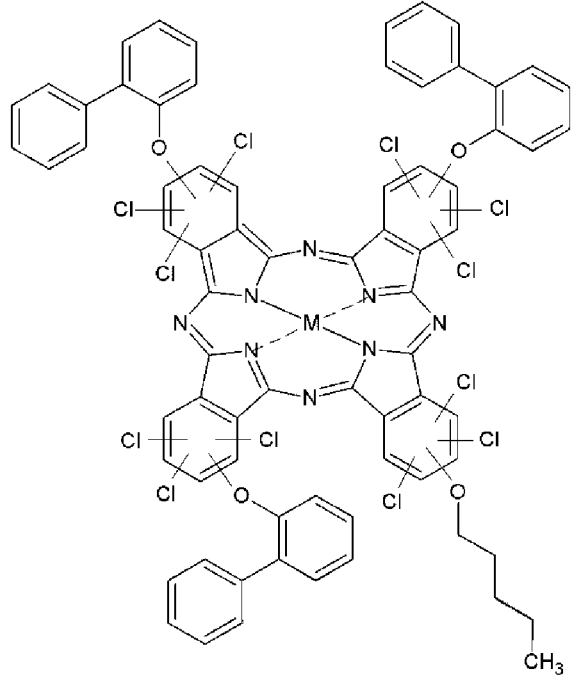

Column 8, Chemical Formula 4 is depicted as:

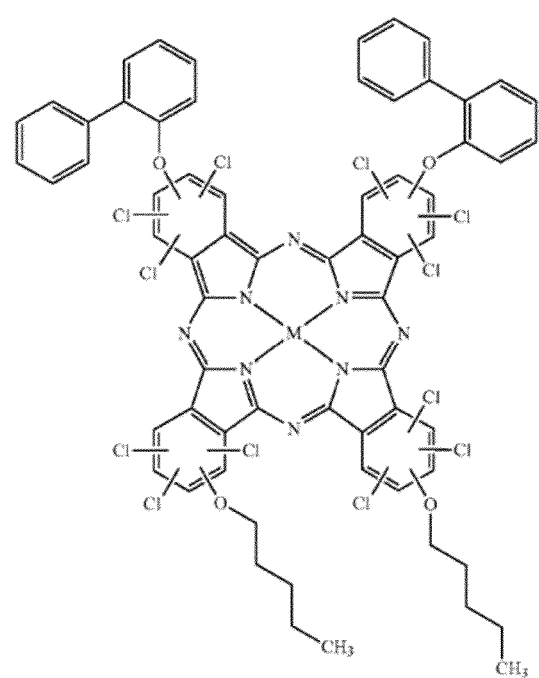

and should be depicted as:

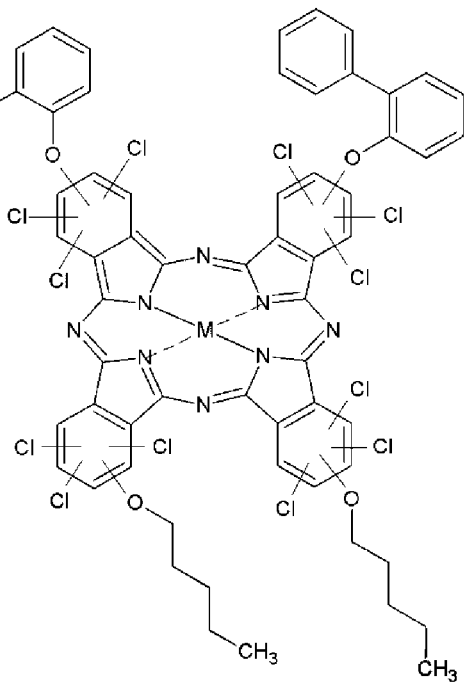

CERTIFICATE OF CORRECTION (continued)

U.S. Pat. No. 9,242,990 B2

In the Specification

Column 9, Chemical Formula 5 is depicted as:    and should be depicted as:

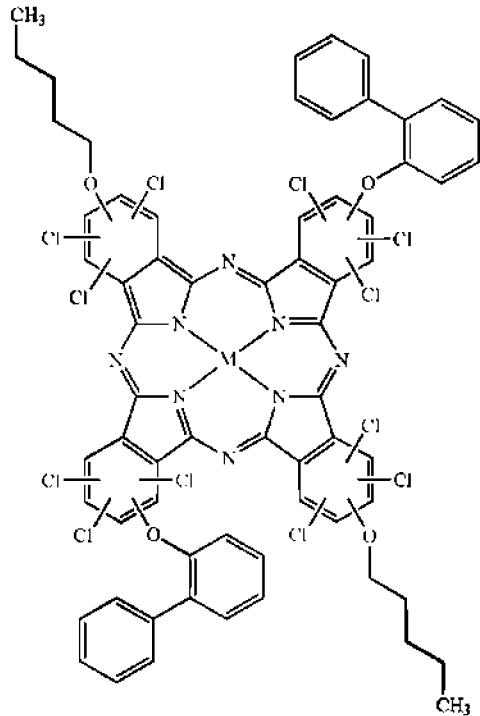 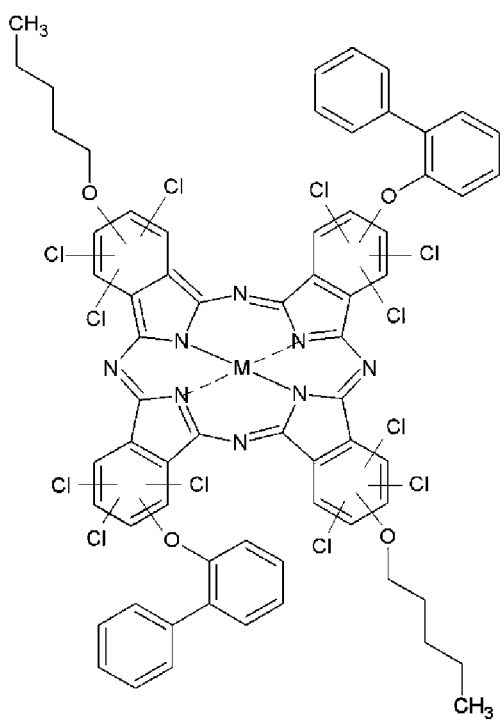

Column 9, Chemical Formula 6 is depicted as:    and should be depicted as: